United States Patent [19]

Lenhoff et al.

[11] Patent Number: 4,506,009

[45] Date of Patent: Mar. 19, 1985

[54] HETEROGENEOUS IMMUNOASSAY METHOD

[75] Inventors: Howard M. Lenhoff, Costa Mesa; That T. Ngo, Irvine, both of Calif.

[73] Assignee: University of California, Berkeley, Calif.

[21] Appl. No.: 363,481

[22] Filed: Mar. 30, 1982

[51] Int. Cl.$^3$ .................. G01N 33/54; C12N 9/96
[52] U.S. Cl. ............................ 435/7; 435/188;
435/810; 436/515; 436/529; 436/535; 436/536;
436/537; 436/538; 436/539; 436/540; 436/541;
436/542
[58] Field of Search ............. 435/4, 7, 188, 810;
436/514, 515, 536, 538, 539, 540, 541, 529, 518,
535, 537, 808, 542

[56] References Cited

U.S. PATENT DOCUMENTS

| | | | |
|---|---|---|---|
| 3,654,090 | 4/1972 | Schuurs et al. | 435/7 |
| 3,791,932 | 2/1974 | Schuurs et al. | 435/7 |
| 3,839,153 | 10/1974 | Schuurs et al. | 435/7 |
| 3,850,752 | 11/1974 | Schuurs et al. | 435/7 |
| 3,879,262 | 4/1975 | Schuurs et al. | 435/7 |
| 3,935,074 | 1/1976 | Rubenstein et al. | 436/537 |
| 4,130,462 | 12/1978 | Rubenstein et al. | 436/537 |
| 4,134,792 | 1/1979 | Boguslaski et al. | 435/7 |
| 4,193,983 | 3/1980 | Ullman et al. | 436/537 |
| 4,288,237 | 10/1980 | Hevey et al. | 435/188 |
| 4,298,685 | 11/1981 | Parikh et al. | 435/7 |
| 4,299,916 | 11/1981 | Litman et al. | 435/805 X |
| 4,374,925 | 2/1983 | Litman et al. | 435/810 X |

Primary Examiner—Esther M. Kepplinger
Attorney, Agent, or Firm—Poms, Smith, Lande & Rose

[57] ABSTRACT

A conjugate useful in determining the amount of antigen or antibody in a liquid sample, said conjugate having a marker, an immunoreactive component (i.e. antigen or antibody) bound to the marker and an insolubilizing binding component which is also bound to the marker. The insolubilizing binding component portion of the conjugate will react with an insolubilizing receptor to form a solid product of conjugate and receptor unless the conjugate reacts with the corresponding antigen or antibody to be analyzed in which event the conjugate will not react with the insolubilizing receptor. The conjugate will be added to a liquid sample containing an unknown amount of, for example, an antibody. A known amount of the corresponding antigen is also added which reacts with both the conjugate and antibody. After the reaction is complete, the liquid sample is contacted with the insolubilizing receptor. Since only the free conjugate reacts with the insolubilizing receptor the amount of antibody originally in the liquid sample can be determined by measuring the activity of the marker in the precipitate.

14 Claims, 1 Drawing Figure

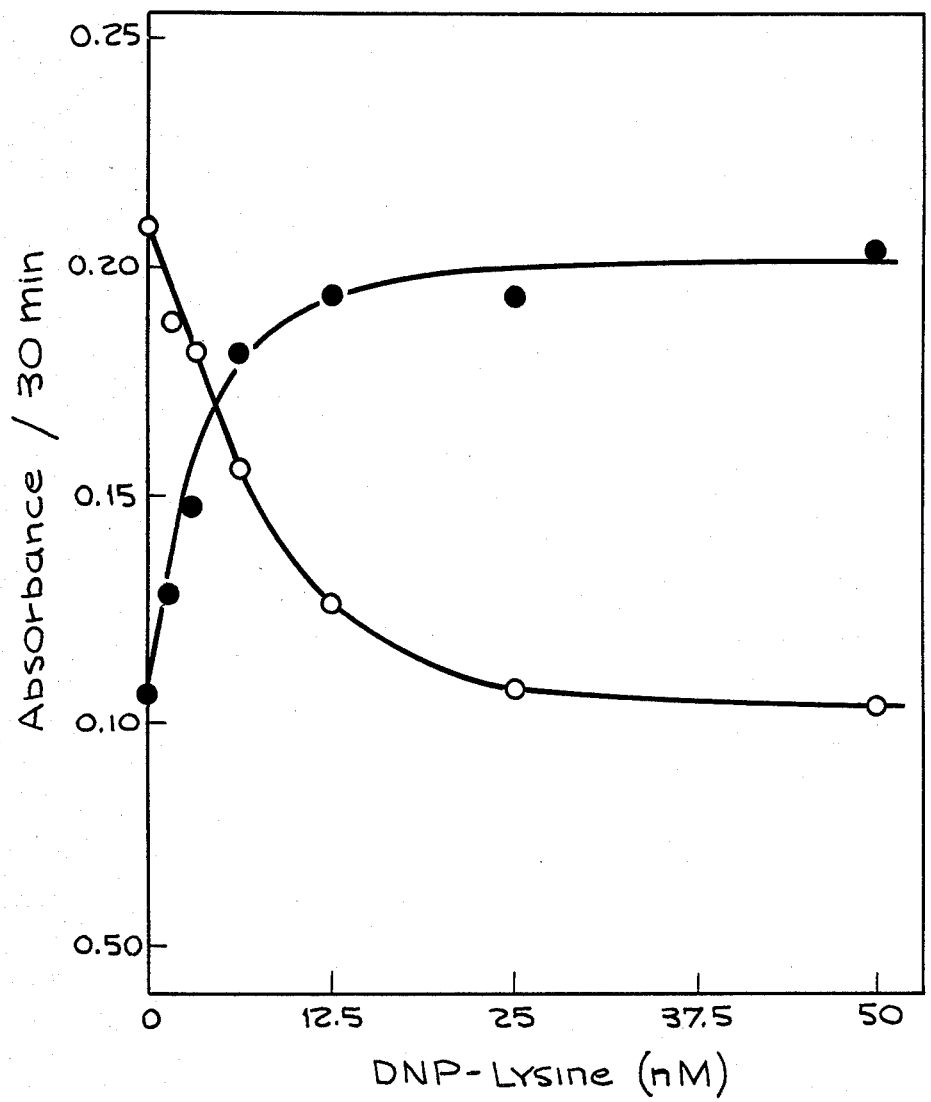

HETEROGENEOUS IMMUNOASSAY METHOD

The invention described herein was made in the course of work under a grant or award from the Department of Health and Human Services.

BACKGROUND OF THE INVENTION

The present invention relates to a novel heterogeneous immunoassay method for determining the amount of antigens (including ligands and other compounds having antigenic sites or determinants) or antibodies. As is known in the art immunoassays are generally of two types, the so-called separation-free or homogeneous immunoassay, i.e. the method does not require the separation of the unreacted or unbound antibody or antigen from the antigen bound to the antibody, and the so-called separation or heterogeneous immunoassay, i.e. this method requires such a separation step.

In the prior art heterogeneous immunoassay methods, the general procedure is to utilize antigen-antibody bindings with either immobilized antigen or antibody as the means to separate the unbound fraction from the bound fraction. The reaction between the antigen and antibody takes place at a solid-liquid interphase because either the antigen or the antibody is immobilized on a solid material. A marker, which is easy to measure quantitatively because of its activity (e.g. the marker may be an enzyme; a fluorescent molecule which emits light upon excitation by an appropriate light source; a chemiluminescent molecule which will emit light after a chemical reaction such as oxidation; a radioactive molecule; etc.) is linked or bound to either the antibody or the antigen. The marker-antibody or antigen conjugate which precipitates or is insolubilized had been complexed with either the corresponding antibody or antigen. This has more than one disadvantage.

Moreover, in the known heterogeneous immunoassay methods the percentage of marker-antigen or antibody conjugate which is insolubilized, decreases as the concentration of the component (either antigen or antibody) which is being analyzed increases. Therefore, the standard curve when using these methods results in a negative slope.

SUMMARY OF THE INVENTION

The present invention, in a relatively simple manner, avoids the problems of the previous heterogeneous immunoassay methods described herein. In particular, in the method and diagnostic kit of the present invention, the insoluble fraction of the marker-antigen or marker-antibody is not derived from the antigen-antibody reaction and therefore is not the basis of the separation step which is, of course, necessary in all heterogeneous immunoassay methods. In the present invention, the marker-antigen or antibody conjugate which is part of the insolubilized phase is completely free of the corresponding antibody or antigen. Moreover, in the present invention, the precipitate having the marker increases in concentration as the concentration of the antigen or antibody to be analyzed increases. Therefore, the standard curve, using the method, diagnostic kit or novel conjugate of the present invention, is a positive slope if the activity of the precipitate is measured.

The present invention is useful to determine the amount of antigen or antibody (hereinafter sometimes referred to as the component to be analyzed) dissolved in a liquid sample. The component to be analyzed is a reactant or component in the reaction of two immunobinding partners (antigen-antibody reaction). The present invention is based, in large part, on a novel conjugate which is added to the liquid sample containing the component to be analyzed. The novel conjugate has three essential components: 1. A marker such as those discussed above with respect to the prior art. 2. An immunoreactive component which has the same immunochemical properties as the component to be analyzed (i.e. either the antigen or antibody) has. 3. An insolubilizing binding component which, when the conjugate is contacted with an insolubilizing receptor, will react with the receptor to form a reaction product which is solid (i.e. insoluble) in the liquid sample containing the antigen or antibody which is the subject of the analysis. However the reactivity of the conjugate for the insolubilized receptor is masked thereby preventing the reaction when the conjugate is contacted by and is bound to the corresponding antibody or antigen which is being analyzed (sometimes referred to as the immunobinding partner of the component to be analyzed). In other words, if the conjugate is in a liquid sample containing an unknown amount of, for example, antibody and the corresponding antigen is added to the liquid sample, the reaction between the antigen and conjugate will prevent the reaction of the conjugate with the insoluble receptor. If, thereafter, the liquid sample is contacted with an insolubilizing receptor, only the free conjugate (i.e. the conjugate which, in the example, is not bound or reacted with the antigen) will react with the insolubilizing receptor and only the free conjugate will form a solid phase and be capable of being separated from the liquid phase by known solid-liquid separation techniques.

The method of the present invention may be generally described as follows:

A liquid sample containing an unknown amount of e.g., antibody, is used. To this sample is added a conjugate composed of (i) a marker, (ii) an immunoreactive component which has the same immunochemical properties as the antibody, and (iii) the insolubilizing binding component. To this solution is added the corresponding antigen to the antibody which is being analyzed to form a reaction mixture. The antigen, of course, reacts competitively with the antibody and the conjugate; the more antibody present the less antigen reacts with the conjugate. After the reaction is completed, the liquid sample is contacted with an insolubilizing receptor. Only the free conjugate reacts with the insolubilizing receptor. The reaction forms a solid precipitate which can be separated from the liquid phase. The amount of marker in the precipitate can be measured using the activity of the marker. The more precipitate which is formed the greater the amount of the antibody in the liquid sample since the product which is precipitated is the conjugate which did not react with the antigen.

In addition to the method just described, the present invention also provides a diagnostic kit for determining the amount of a component to be analyzed (i.e. the antigen or antibody). The kit will include the conjugate previously described, as well as the insolubilizing receptor, both separate, one from the other. In addition, the kit may also include the corresponding antibody or antigen to the component being analyzed. The conjugate, apart from the method and kit, is also considered novel.

DESCRIPTION OF THE PREFERRED EMBODIMENTS

The method, kit and conjugate of the instant invention are presently believed to be useful in determining the amount of any antigen or antibody. Particular antigens and antibodies to which the present invention is believed to be well adapted include: hormones; steroids such as progesterone, etc.; vitamins; histamine; antibiotics; and various viruses such as hepatitis.

Markers useful in the present invention are well known in the art and therefore no detailed description will be given. Of course, markers whose activity is easily determined and measured are the most desirable. Such markers include radioactive substances such as radio-iodine, etc. Another marker particularly useful in the present invention are enzymes, particularly those enzymes which are simple to determine by, for example, colorimetry, spectrophotometry, fluorospectrophotometry and gasometry. In order to form the conjugate of the present invention, the marker, e.g. the enzyme must be coupled to the antigen or antibody. Existing side chains may be used for such coupling but if they do not exist on either the marker or antigen or antibody such may be supplied using polyvalent compounds such as di- or triisocyanates, polyaldehydes such as glutaraldehyde, hydrazines, etc.

Enzymes which may be used in the present invention include peroxidase, $\beta$-galactosidase, beta-glucuronidase, urease, catalase, glucose oxidase, dehydrogenase, etc.

The insolubilizing binding component is bound to the marker, e.g. the enzyme either by side chains of the enzyme or, by side chains on the insolubilizing binding component, or the immunoreactive component. If none of the components of the conjugate have the necessary side chains such may be added using, e.g. the polyvalent compounds as previously discussed herein.

In addition to the foregoing, the insolubilizing binding component of the instant conjugate must be able to react with the insolubilizing receptor to form an insoluble reaction product in the liquid sample which can be easily separated from the liquid phase using known solid-liquid separation techniques, e.g. centrifugation. One of the most important features, however, is the masking of the insolubilizing binding component's ability to react with the insolubilizing receptor when the antigen or antibody binds to the immunoreactive component of the conjugate. Thus, the insolubilizing binding component, after reaction with the marker to form the conjugate, will contain a group or groups reactive with the insolubilizing receptor but which will be masked or deactivated by the antibody or antigen which is bound to the immunoreactive component. The insolubilizing binding component may be any molecule which has a high and specific affinity for an insolubilizing receptor and which is stearically hindered by the immunobinding partner's immunoreaction with the immunoreactive component of the conjugate. By "high affinity" is meant that the insolubilizing receptor and insolubilizing binding component have a binding constant of at least about $10^6$ molar and preferably about at least $10^9$ molar. For example, haptens capable of inducing high affinity antibodies are useful as insolubilizing binding components in the instant invention. Exemplary haptens meeting the foregoing criteria are those having an azobenzene immunoreactive group such as diazotized sulfonilic acid in which case the insolubilizing receptor would be its corresponding immobilized antibody.

The insolubilizing receptor is chosen so that it will react with the insolubilizing binding component. A particular insolubilizing receptor, for example, can be a "universal" receptor because it may be used with any antibody or antigen as long as the marker is bound to the same insolubilizing binding component, which can be easily accomplished by use of the polyvalent compounds previously described. For example, avidin, which is a 70 kilodalton protein in egg white, is an excellent insolubilizing receptor, particularly when used with biotin as the insolubilizing binding component, because avidin has a very high affinity (about $10^{15}$ molar) for biotin. In this regard it should be noted that the roles of biotin and avidin may be easily reversed. The avidin may be the insolubilizing binding component and the immobilized biotin may be the insolubilizing receptor.

The separation step of the liquid and solid phase, which, in common with all heterogeneous immunoassay methods is required in the method of the present invention, is easily accomplished by means known in the art, e.g. centrifugation. However, this step may be eliminated by using a tube coated with insolubilizing receptor or by using a column or insolubilizing receptor which is insoluble in the liquid sample.

In the method of the present invention, one will use predetermined amounts of the conjugate, immunobinding partner and insolubilizing receptor. The amount of immunobinding partner of the component to be analyzed which is present in the liquid sample containing the conjugate and component to be analyzed should be less than that which would be necessary to react with all of the conjugate, i.e. there should be free or unreacted conjugate after the reaction of the binding partner with the conjugate.

It should also be noted that the reaction product of the immunobinding partner and the conjugate should be soluble in the liquid sample.

The amount of insolubilizing receptor is not particularly important except there should be a sufficient amount present to react with all of the free conjugate in the liquid sample, i.e. there should be a stoichiometric excess based on the amount of unreacted or free conjugate in the liquid sample.

In the following preferred exemplary embodiments, the enzyme used is beta-galactosidase, the insolubilizing component is activated biotin (N-hydroxysuccinimido biotin), the antigen is DNP-lysine, and the insolubilizing receptor is avidin immobilized on AH-Sepharose. Avidin was immobilized on AH-Sepharose using glutaraldehyde as a crosslinker. Washed AH-Sepharose (10 ml) was suspended in 400 ml 5% glutaraldehyde in 0.2 M NaHCO$_3$, pH 8.5. The suspension was stirred for 1 hour (h) at room temperature (RT), after which the gel was washed successively with 0.5 liters of 0.5 M NaCl and 0.5 liters of 0.1 M NaHCO$_3$, pH 8.5. The glutaraldehyde activated gel was suspended in 5 ml of avidin (50 mg in 5 ml of 0.1 M NaHCO$_3$, pH 8.5), the suspension was stirred at RT for 1 h and at 4° C. for 20 h. The avidin gel conjugate was washed sequentially with 1 liter of 0.5 M NaCl in 0.1 M sodium phosphate, pH 8.0 and 1 liter of 0.1 M sodium phosphate, pH 8.0. The amount of avidin bound was 13 mg/10 ml packed gel.

The immunoreactive component was m-maleimidobenzoyl-DNP-lysine which was made as follows:

Ten μmoles of m-maleimidobenzoyl-N-hydroxysuccinimide ester and 11 μmoles of Na$_2$CO$_3$ were added to a 2 ml. mixture of tetrahydrofuran and dimethylformamide (1:1 volume mixture) and stirred at room temperature. The reaction was complete in 24 hours.

The enzyme, which has both free amino and thiol groups, was reacted with the activated biotin as follows: Beta-galactosidase was dialzed against 0.1 M sodium phosphate, pH 8.0. To the dialyzed enzyme (2.8 nmoles in 2 ml of 0.1 M phosphate, pH 8.0) was added 281 nmoles N-hydroxysuccinimide-biotin in 0.1 ml dimethylsulfoxide. The solution was stirred at room temperature for 3 h and at 4° C. for 5 h, and then dialyzed at 4° C.

The resulting biotinyl-enzyme was reacted with m-maleimidobenzoyl-DNP-lysine as follows: To 1 ml biotinyl enzyme (1.5 nmoles) was added 0.2 ml m-maleimidobenzoyl-DNP-lysine (1 μmole). The solution was stirred at room temperature for 2 h. The excess unreacted m-maleimidobenzoyl-DNP-lysine was separated from the labeled enzyme on a column (2×45 cm) of Sephadex G-50 C. The eluant was 0.1 M sodium phosphate, pH 7.2.

The final product is the conjugate of the present invention and each enzyme molecule is linked to 21 biotin tags and 37 DNP-lysines.

EXAMPLE 1

BINDING OF CONJUGATE TO AVIDIN

Varying amounts of 10% avidin-gel suspension were added to 200 μliters beta-galactosidase linked to DNP-lysine and biotin (1.36 nM). The suspensions were adjusted to 600 μliters with 0.5% gelatin in 0.1 M sodium phosphate, pH 7.2 and incubated at 25° C. for 30 min. The suspensions were centrifuged for 5 min. using an Eppendorf centrifuge. The supernatants (500 μliters were assayed for beta-galactosidase activity using o-nitrophenyl-beta-galactopyranoside as the substrate. The pellets after centrifugation were washed by suspending them in 1 ml of 0.5% gelatin in 0.1 M sodium phosphate, pH 7.2 followed by centrifugation for 5 min. The washing was repeated three times. The final pellets were assayed for enzyme activity by suspending them in 3 ml substrate solution of o-nitrophenyl-beta-galactopyranoside. All assays were incubated at 25° C. for 30 min.

An addition of increasing amounts of avidin-gel, i.e. the insolubilized receptor, to a fixed concentration of the conjugate gave a decrease in enzyme activity in the supernatant fraction and a concommitant increase in enzyme activity in the solid fraction.

EXAMPLE 2

Adding Anti-DNP Serum to Conjugate

Antibody to DNP-lysine prevents the beta-galactosidase linked to DNP-lysine and biotin from binding to avidin-gel. Varying amounts of anti-DNP serum were added to 200 μliters beta-galactosidase linked to DNP-lysine and biotin (1.36 nM). The solutions were adjusted to 600 μliters. Constant amounts of 10% avidin-gel suspension (400 λ) were added. The mixtures were incubated at 25° C. for 30 min. and were centrifuged for 5 min. The supernatants (800 μliters) were assayed for enzyme activities. The pellets were washed three times and assayed for activities as described in Example 1.

Addition of increasing amounts of anti-DNP-serum and fixed amounts of avidin-gel to a solution containing the conjugate gave an increase in enzyme activity in the supernatant fraction and concommitant decrease in enzyme activity in the solid fraction. This demonstrates that the antibodies were bound to the DNP-residue of the conjugate and that the resultant antibody-conjugate complex was not able to bind to the insolubilizing receptor.

EXAMPLE 3

Standard Curve for Measuring DNP-Lysine

Solutions of 200 μliters solutions containing a fixed concentration of beta-galactosidase linked to DNP-lysine and biotin (1.36 nM). To these solutions were added 0.5 μliter anti-DNP serum and 500 μliters 10% avidin-gel suspension. The mixtures were incubated at 25° C. for 30 min. and centrifuged for 5 min. The supernatants (800 μliters)were assayed for enzyme activity. The pellets were washed three times and assayed for enzyme activity.

The results of this example are shown in the drawing wherein the open circles show the enzyme activity of the liquid (supernatant) phase and the closed circles show the enzyme activity of the solid phase.

Example 3 demonstrates that DNP-lysine residues of the conjugate competed successfully for the antibodies with the free analyte DNP-lysine. When increasing amounts of DNP-lysine were added to fixed amounts of conjugate, antibody and avidin-gel, the enzyme activity in the supernatant decreased while simultaneously that in the insoluble fraction increased (FIG. 1). By having DNP-lysine compete with immunoreactive components of the conjugate for antibodies, there is more conjugate uncomplexed with antibody and free to bind to the insolubilized receptor. Thus, using the curve presented in the drawing, the concentration of analyte, DNP-lysine in the range of 1-25 nM can be measured.

We claim:

1. A heterogeneous immunoassay method for determining the amount of a component to be analyzed, said component to be analyzed being a component in the reaction of two immunobinding partners, one of said immaunobinding partners being an antigen and one of said immunobinding partners being an associated antibody, said component to be analyzed being dissolved in a liquid sample, which comprises:

providing a liquid sample containing a reaction mixture dissolved therein, said reaction mixture consisting essentially of (a) an undetermined amount of said component to be analyzed, (b) a conjugate of (i) a marker, (ii) an immunoreactive component bound to said marker and having the same immunochemical properties of said component to be analyzed and (iii) an insolubilizing binding component bound to said marker and which contains a group reactive with an insolubilizing receptor to react with said insolubilizing receptor to form a solid phase in said liquid sample, said insolubilizing receptor and said insolubilizing binding component having a binding constant of at least about 10$^9$ molar, the reactivity of said group of said insolubilizing binding component for said insolubilizing receptor being deactivated when said immunobinding partner immunoreacts with said immunoreactive component of said conjugate, and (c) a predetermined amount of said immunobinding partner of the component to be analyzed, said predetermined amount being such that there is a certain amount of unreacted conjugate remaining in said liquid sample;

allowing said liquid sample to incubate until the reaction is complete between said immunobinding partner and said component to be analyzed and said immunobinding partner and said conjugate, the reaction product of said immunobinding partner and said conjugate being soluble in said liquid sample;

contacting said liquid sample after said reaction is complete with a stoichiometric excess, based on the amount of unreacted conjugate in said liquid sample of said insolubilizing receptor and allowing the reaction between said insolubilizing receptor and said unreacted conjugate to go to completion and form a solid precipitate;

separating said solid phase from said liquid sample; and determining the quantity of said component to be analyzed by measuring the activity of the marker in either the solid phase or the liquid sample.

2. A heterogeneous immunoassay method according to claim 1 wherein said marker is an enzyme.

3. A heterogeneous immunoassay method according to claims 1 or 2 wherein said component to be analyzed is an antigen and said immunobinding partner of said component to be analyzed is an antibody.

4. A heterogeneous immunoassay method according to claim 1 wherein said insolubilizing binding component is biotin.

5. A heterogeneous immunoassay method according to claim 4 wherein said insolubilizing receptor is avidin.

6. A diagnostic kit for determining the amount of a component to be analyzed when said component to be analyzed is dissolved in a liquid sample, said component to be analyzed being a component in the reaction of two immunobinding partners, one of said immunobinding partners being an antigen and one of said immunobinding partners being an associated antibody, said diagonstic kit consisting essentially of:

a separate conjugate of (i) a marker, (ii) an immunoreactive component bound to said marker and having the same immunochemical properties of said component to be analyzed and (iii) an insolubilizing binding component bound to said marker, which contains a group reactive with an insolubilizing receptor to react with said receptor to form a solid reaction product which is insoluble in said liquid sample, said insolubilizing receptor and said insolubilizing binding component having a binding constant of at least $10^9$ molar, the reactivity of said group of said insolubilizing binding component for said insolubilizing receptor being capable of being deactivated when said conjugate is contracted with the immunobinding partner of the component to be analyzed;

a separate immunobinding partner of the component to be analyzed; and a separate insolubilizing receptor wherein said amount of said immunobinding partner is less than that amount which would react with all of said quantity of said conjugate and said quantity of insolubilizing receptor is a stoichiometric excess of the quantity of unreacted conjugate in said liquid sample.

7. A diagnostic kit according to claim 6 wherein said marker is an enzyme.

8. A diagnostic kit according to claim 7 wherein said component to be analyzed is an antigen and said immunobinding partner of the component to be analyzed is an antibody.

9. A diagnostic kit according to claim 6 wherein said insolubilizing binding component is biotin.

10. A diagnostic kit according to claim 9 wherein said insolubilizing receptor is avidin.

11. A conjugate for use in determining the amount of a component to be analyzed when said component to be analyzed is dissolved in a liquid sample, said component to be analyzed being a component in the reaction of two immunobinding partners, one of said immunobinding partners being an antigen and one of said immunobinding partners being an associated antibody, said conjugate consisting essentially of (i) a marker, (ii) an immunoreactive component bound to said marker and having the same immunochemical properties of said component to be analyzed and (iii) an insolubilizing binding component bound to said marker and which contains a group reactive with an insolubilizing receptor to react with said receptor to form a solid reaction product which is insoluble in said liquid sample, said insolubilizing receptor and said insolubilizing binding component having a binding constant of at least about $10^9$ molar, the reactivity of said group of said insolubilizing binding component for said insolubilizing receptor being capable of being deactivated when said conjugate is contacted with the immunobinding partner of the component to be analyzed.

12. A conjugate according to claim 11 wherein said marker is an enzyme.

13. A conjugate according to claim 11 wherein said insolubilizing binding component is biotin.

14. A conjugate according to claim 11 wherein said insolubilizing binding component is avidin.

* * * * *